United States Patent [19]

Martini

[11] 4,118,421
[45] Oct. 3, 1978

[54] PROCESS FOR THE MANUFACTURE OF PERFLUORO-ALKOXY-PROPIONIC ACID FLUORIDES

[75] Inventor: Thomas Martini, Bad Soden am Taunus, Fed. Rep. of Germany

[73] Assignee: Hoechst Aktiengesellschaft, Frankfurt am Main, Fed. Rep. of Germany

[21] Appl. No.: 808,537

[22] Filed: Jun. 21, 1977

[30] Foreign Application Priority Data

Jun. 23, 1976 [DE] Fed. Rep. of Germany ....... 2627986

[51] Int. Cl.$^2$ .............................................. C07C 51/58
[52] U.S. Cl. ................................................. 260/544 F
[58] Field of Search ...................................... 260/544 F

[56] References Cited

U.S. PATENT DOCUMENTS 3,250,808  5/1966  Moore et al. ................... 260/535
3,321,532  5/1967  Lorenz ............................ 260/614
3,322,826  5/1967  Moore ............................. 260/544

FOREIGN PATENT DOCUMENTS 707,361    4/1965   Canada ............................. 260/544
1,520,527  1/1969   Fed. Rep. of Germany.
1,292,268  10/1972  United Kingdom ............... 260/544

Primary Examiner—Gerald A. Schwartz
Attorney, Agent, or Firm—Curtis, Morris & Safford

[57] ABSTRACT

Perfluoro-alkoxy propionic acid fluorides may be obtained by reacting hexafluoro-propene epoxide with a perfluoro-carboxylic fluoride in an aprotic polar solvent in the presence of a N,N,N', N'-tetrasubstituted diaminodifluoromethane as catalyst.

The compounds obtained may be used as starting products for valuable perfluoro ethers which are highly inert towards heat or aggressive chemicals, such as fluorine.

6 Claims, No Drawings

PROCESS FOR THE MANUFACTURE OF PERFLUORO-ALKOXY-PROPIONIC ACID FLUORIDES

The manufacture of perfluoro-alkoxy-propionic acid fluorides by addition of hexafluoropropene epoxide, especially oligomers of hexafluoropropene epoxide (HFPO), on perfluorocarboxylic acid fluorides in the presence of catalysts is known. According to German Offenlegungsschrift No. 1,520,527, alkali metal fluorides such as caesium fluoride are especially suitable catalysts. According to this process, linear polyethers having a broad molecular weight distribution range are obtained.

Canadian Patent Specification No. 707,361 describes the dimerization and trimerization of HFPO at 10° to 17° C under normal pressure in the presence of caesium fluoride as catalyst. In this case, however, the high reaction temperatures require a very slow and dosed feed of the epoxide to be reacted.

Also according to German Offenlegungsschrift No. 1,520,527, HFPO may be dimerized in a selective manner by maintaining it at a temperature of −15° to −5° C in the presence of dimethyl aniline, or when it is treated according to Belgian Patent Specification No. 751,076 in acetonitrile with silver nitrate as catalyst. Generally, the HFPO polymerization yields products having a high molecular weight and/or a broad molecular weight distribution. Trimers, tetramers, pentamers are therefore obtained by distillation separation only, and the generally undesirable high molecular weight amounts occurring cannot be prevented to be formed.

The present invention now provides a process for the manufacture of perfluoro-alkoxy-propionic acid fluorides of the formula

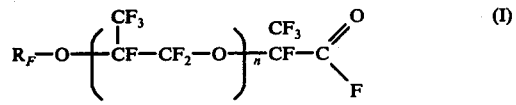

wherein $R_F$ is a perfluoro-alkyl radical having from 1 to 8, preferably 2 to 3, carbon atoms, and $n$ is 0, 1 or 2, by catalytic addition of hexafluoropropene epoxide on perfluorocarboxylic acid fluorides of the formula

wherein $R_F$, is fluorine or a perfluorinated hydrocarbon radical having from 1 to 7, preferably 1 or 2, carbon atoms, which comprises carrying out the addition in an aprotic polar solvent at tempertures of from −50° to +20° C in the presence of compounds of the formula

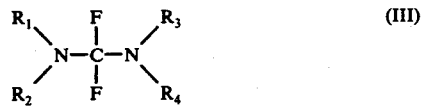

wherein $R_1$ through $R_4$ are alkyl radicals having from 1 to 4 carbon atoms, and two of these radicals linked to the same nitrogen atom may form a five- or six-membered ring which may be interrupted once by members of the following groups: —O—, >N—($C_1$-$C_4$)-alkyl or >N—$CF_2$H.

It is especially advantageous to use perfluoropropionic acid fluoride as perfluorocarboxylic acid fluoride (II), which compound is obtained in situ from HFPO under the above reaction conditions. This means that the reaction according to this invention includes also the oligomerization of HFPO.

The catalysts of formula (III) used in the reaction are formed in situ by reaction of HFPO with a compound of the formula

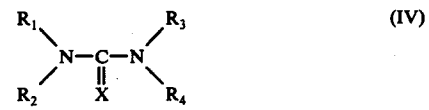

wherein X may be O or S and $R_1$ through $R_4$ are as defined above. This catalyst may be prepared either directly in the reaction mixture or previously in a special reaction step.

Preferred radicals $R_1$ through $R_4$ are alkyl radicals having 1 or 2 carbon atoms, or, in the case of

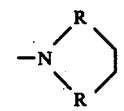

cyclic groups such as pyrrolidine, piperidine, N-methyl-piperazine, N-formyl-piperazine or morpholine radicals. The catalyst most preferred for the reaction of the invention is bis-dimethyl-amino-difluoromethane.

The compounds of formula (III) are obtained by reacting the corresponding ureas of formula (IV) with HFPO at the above reaction temperatures, optionally in an aprotic polar solvent or in molten urea, in which reaction the carbonyl group is converted to the —$CF_2$— group and HFPO to perfluoro-pyruvic acid fluoride. This reaction proceeds according to the following scheme

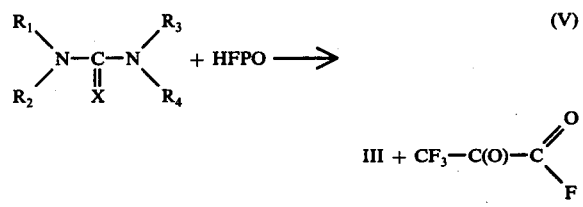

The perfluoro-pyruvic acid fluoride so obtained, together with one and two further molecules of HFPO, respectively, forms perfluoro-2-oxo-3,6-dimethyl-1,4-dioxan (VI) and perfluoro-α-(3,6-dimethyl-1,4-dioxa-nyl-2-oxy)-propionic acid fluoride (VII), respectively.

The catalyst (III) so obtained may be separated by fractional distillation; however, it may be applied without isolation as well. Cyclization of the perfluoropyruvic acid fluoride (V) formed with further HFPO proceeds in such a rapid manner that, after the reaction is complete, the compound (V) is either completely absent or present in insignificant amounts only. When the reaction solution containing the catalyst is used for the further reaction of HFPO, the compound (VI) (dioxan) too is converted practically completely to perfluoropropionic acid fluoride (VII), the presence of which generally does not disturb the application of the products obtained in accordance with this invention. On the other hand, the catalyst of formula (III) may be prepared alternatively according to J. Am. Chem. Soc. 84 (1962), 4275, from a compound of formula (IV) and $COF_2$, and then applied in pure form.

The catalyst is generally used in amounts of from 0.01 to 0.5, preferably 0.05 to 0.3, mol per 100 ml of solvent. Larger amounts may be employed but do not bring about further advantages.

When the corresponding urea of formula (IV) is used for preparing the catalyst in situ, the same or a somewhat higher molar amount of (IV), that is, up to the double molar amount, preferably a 1.2 to 1.5-fold molar amount, relative to the intended catalyst concentration, is employed.

The reaction temperatures required for the oligomerization are from $-50°$ to $+20°$ C, preferably from $-40°$ to $+5°$ C, and especially from $-30°$ to $-10°$ C.

The amount of solvent is not critical in principle, since the oligomers of HFPO formed are nearly insoluble in the polar aprotic solvents used and precipitate as second phase, which is generally the heavier one. However, since the solvent on the other hand is not completely insoluble in the oligomer phase and may be partially dispersed in it with the necessary thorough agitation, it is recommended to use about 50 to 500, preferably 100 to 200, ml of an aprotic polar solvent per 1000 g of reacted or unreacted HFPO. Suitable solvents of this kind are for example ethers such as ethyleneglycol, diethyleneglycol, tetra-ethyleneglycol dimethyl ether, diethyleneglycol diethyl ether, or nitriles such as acetonitrile or propionitrile, which may be diluted by inert unpolar solvents such as pentane, hexane, cyclohexane, or fluorine containing alkanes such as trifluoro-trichloro-ethane, without substantially interfering with the reaction or adversely affecting the degree of oligomerization. This dilution may be carried out using up to two, preferably up to one, part by volume.

Generally, the process of the invention is carried out as follows: Solvent, perfluorocarboxylic acid fluoride and catalyst are introduced into the reactor and HFPO is fed in subsequently at reaction temperature. When the reaction is started from perfluoropropionic acid fluoride prepared in situ, that is, from HFPO alone, a preferred embodiment of the present invention comprises introducing catalyst, solvent and simultaneously HFPO into the reactor, or introducing catalyst and solvent and feeding in subsequently HFPO at reaction temperature. Alternatively, solvent and epoxide may be introduced and the catalyst (for example tetramethyl urea) may be added dropwise and slowly.

The degree of addition obtained is from 1 to 5, preferably from 2 to 4, and correspondingly, the degree of oligomerization is from 2 to 6, preferably from 3 to 5, depending on the reaction conditions. Dimers are substantially obtained when operating in the upper range of temperatures (0° to 20° C) and with high epoxide concentration, especially in the case of the epoxide being introduced under autogenous pressure before the start of the reaction. Trimers to pentamers are obtained substantially at low temperatures ($-15°$ to $-30°$ C) and lower epoxide concentration, especially when the epoxide is fed in in gaseous form under about atmospheric pressure.

Work-up is generally carried out by distillation, that is, unreacted HFPO and HFP present are distilled off first, subsequently the oligomer phase is separated and subjected to fractional distillation. The solvent phase containing the catalyst is reused for further reactions.

The following examples illustrate the invention.

EXAMPLE 1

15 g of bis-dimethylamino-difluoromethane and 75 ml of tetra-ethyleneglycol dimethyl ether are introduced into a flask provided with agitator, gas inlet tube, intense cooling ($CO_2/CH_2Cl_2$), thermometer and cooling bath, and 500 g of a mixture of HFPO and hexafluoropropene (HFP) in a weight ratio of 65:35 are fed in within 18 hours at $-30°$ to $-25°$ C. Subsequently, agitation is continued for a further 18 hours. After heating to room temperature and separation of the heavier phase, 450 g of crude oligomer (containing HFP) are obtained which are worked up by distillation. Result:

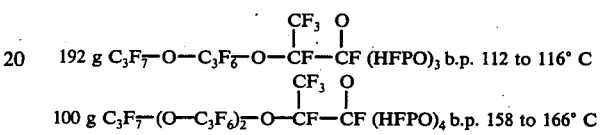

residue 20 g.

EXAMPLE 2

1000 g of a mixture of HFPO/HFP (weight ratio 1:1) are fed in at a dosage rate of 15 to 20 l/h and a temperature of $-30°$ to $-25°$ C to a solution of 50 g of TMU in 100 ml of tetra-ethyleneglycol dimethyl ether in an apparatus as described in Example 1, and the batch is then agitated for a further 10 hours at $-25°$ C. Subsequently, the reaction mixture is heated to room temperature and the heavier phase which separates is distilled.

34 g $(HFPO)_2$ b.p. 52° to 56° C
249 g $(HFPO)_3$
156 g $(HFPO)_4$
residue 37 g are obtained.

A similar result is obtained when 25 g of tetramethyl urea are used.

EXAMPLE 3

To 15 g of tetramethyl thiourea and 100 ml of diethyleneglycol diethyl ether, 600 g of a HFPO/HFP mixture (weight ratio 65:35) are added according to Example 2 at a dosage rate of 15 l/h and at $-25°$ to $-20°$ C. Subsequently, agitation is continued for a further 2 hours at $-20°$ C. After heating and degassing of the HFP inert under the reaction conditions, the precipitated lower phase is washed with 300 ml of acetonitrile and distilled.

50 g $(HFPO)_2$
157 g $(HFPO)_3$
87 g $(HFPO)_4$
residue 18 g are obtained.

EXAMPLE 4

50 ml of trifluoro-trichloro-ethane, 50 ml of tetraglyme and 50 g of tetramethyl urea are introduced into an apparatus as described in Example 1, and 620 g of a HFPO/HFP mixture (weight ratio 70:30) are fed in subsequently at $-25°$ to $-30°$ C at a dosage rate of 5 - 10 l/h. Agitation is continued for a further 3 hours, and the heavier phase isolated, washed with 300 ml of acetonitrile and distilled.

First runnings up to 46° C
45 g 173 g (HFPO)$_4$
191 g (HFPO)$_5$
residue 19 g are obtained.

EXAMPLE 5

As described in Example 1, 20 g of bis-dimethylamino-difluoromethane are added to a mixture of 30 ml of trifluoro-trichloro-ethane and 30 ml of tetra-ethyleneglycol dimethyl ether, and 400 g of 80 – 85% HFPO are fed in within 16 hours at −30° to −25 ° C. Subsequently, agitation is continued for a further 2 hours, the heavier phase which precipitates is washed with 100 ml of acetonitrile, and subsequently distilled (394 g).

21 g (HFPO)$_2$
124 g (HFPO)$_3$
147 g (HFPO)$_4$
40 g higher oligomerized material are obtained.

EXAMPLE 6

1800 g of a mixture of 70% HFPO and 30% of HFP are fed, at −25° to −20° C and a dosage rate of 15 to 20 l/h, to a solution of 232 g of tetramethyl urea in 200 ml of tetra-ethyleneglycol dimethyl ether in an apparatus as described in Example 1. Subsequently, agitation is continued for 4 hours, and the temperature is raised to room temperature. The two phases which have formed are separated, and the upper phase is distilled at 40° – 50° C under reduced pressure of 5 mm Hg. The material which escapes (43 g) is collected in a cooling trap and distilled again. Besides first runnings having a boiling point of 72° – 100° C (15.5 g) and a reflux of 10 g, 17.5 g of bis-dimethylamino-difluoromethane having a boiling point of 100° to 103° C are obtained, identified by $^1$H-NMR, $^{19}$F-NMR and IR spectrum.

The residue remaining after this distillation under reduced pressure is distilled for its part. 171 g of unreacted tetramethyl urea are recovered.

Distillation of the fluoro-organic phase yields
50 g (HFPO)$_2$
480 g (HFPO)$_3$
482 g (HFPO)$_4$
109 g of higher oligomerized material remain as residue.

EXAMPLE 7

100 g of TMU and 150 ml of diethyleneglycol diethyl ether are introduced into an autoclave, and 1700 g of a mixture of HFPO and HFP (weight ratio 70:30) are fed in and condensed. Agitation is continued for 12 hours at 0° to 5° C, and subsequently for a further 12 hours at room temperature. The autoclave is depressurized, thus allowing 439 g of a mixture of HFP and perfluoropropionic acid fluoride (weight ratio 75:25) to escape.

Distillation of the separated oligomers yields:
920 g (HFPO)$_2$
126 g of higher oligomerized material.

What is claimed is:

1. A process for the manufacture of perfluoro-alkoxy-propionic acid fluorides of the formula

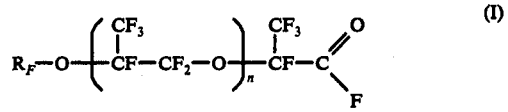

wherein $R_F$ is a perfluoro-alkyl radical having from 1 to 8 carbon atoms, and $n$ is 0, 1 or 2, by catalytic addition of hexafluoropropene epoxide to perfluorocarboxylic acid fluorides of the formula

wherein $R_{F'}$ is fluorine or a perfluorinated hydrocarbon radical having from 1 to 7 carbon atoms, which comprises carrying out the addition in an aprotic polar solvent at temperatures of from −50° to +20° C in the presence of a N,N,N',N'-tetra-alkyl-substituted diaminodifluoromethane as catalyst.

2. A process for the manufacture of perfluoro-alkoxy-propionic acid fluorides of the formula

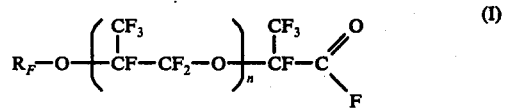

wherein $R_F$ is a perfluoro-alkyl radical having from 1 to 8 carbon atoms, and $n$ is 0, 1 or 2, by catalytic addition of hexafluoropropene epoxide on perfluorocarboxylic acid fluorides of the formula

wherein $R_{F'}$ is fluorine or a perfluorinated hydrocarbon radical having from 1 to 7 carbon atoms, which comprises carrying out the addition in an aprotic polar solvent at temperatures of from −50° to +20° C in the presence of compounds of the formula

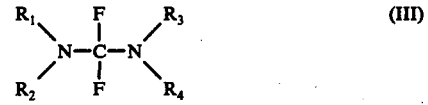

wherein $R_1$ through $R_4$ are alkyl radicals having from 1 to 4 carbon atoms, and two of these radicals linked to the same nitrogen atom may form a five- or six-membered ring which may be interrupted once by members of the following groups: —O—, >N—(C$_1$-C$_4$)-alkyl or >N—CF$_2$H.

3. The process as claimed in claim 2, which comprises using perfluoropropionic acid fluoride as perfluorocarboxylic acid fluoride (II).

4. The process as claimed in claim 3, which comprises producing the perfluoropropionic acid fluoride at temperatures of from −50° to +20° C in the presence of an aprotic polar solvent and of compounds of the formula (III) from hexafluoropropene epoxide.

5. The process as claimed in claim 2, which comprises producing the catalyst of the formula (III), at temperatures of from −50° to +20° C, in liquid phase from an
urea of the formula
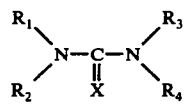
wherein X is O or S and $R_1$ through $R_4$ are as defined in claim 2, by feeding in hexafluoropropene epoxide.
6. The process as claimed in claim 1, which comprises carrying out the addition in the presence of bis-dimethylamino-difluoromethane as catalyst.